(12) United States Patent
Nguyen et al.

(10) Patent No.: US 6,303,784 B1
(45) Date of Patent: Oct. 16, 2001

(54) PHARMACEUTICAL AMINOPHOSPHONIC ACID DERIVATIVES

(75) Inventors: Lan Mong Nguyen, Nyon; Hieu Trung Phan, Tannay, both of (CH); Vinh Van Diep, Vetraz-Monthoux; Simon Floret, Thoiry, both of (FR); Raymond Azoulay, Geneva (CH); Eric Niesor, Nyon (CH); Craig Leigh Bentzen, Bogis-Bossey (CH); Robert John Ife, Stevenage (GB)

(73) Assignees: SmithKline Beecham p.l.c., Middlese (GB); Symphar SA, Geneva (CH)

( * ) Notice: Subject to any disclaimer, the term of this patent is extended or adjusted under 35 U.S.C. 154(b) by 0 days.

(21) Appl. No.: 09/331,385

(22) PCT Filed: Dec. 17, 1997

(86) PCT No.: PCT/EP97/07161

§ 371 Date: Jun. 18, 1999

§ 102(e) Date: Jun. 18, 1999

(87) PCT Pub. No.: WO98/28310

PCT Pub. Date: Jul. 2, 1998

(30) Foreign Application Priority Data

Dec. 20, 1996 (GB) .................................... 9626615

(51) Int. Cl.$^7$ ............................ C07F 9/28; A61K 31/675
(52) U.S. Cl. .............................. 546/24; 546/22; 568/168; 568/169
(58) Field of Search .................... 558/168, 169; 546/22; 514/89

(56) References Cited

U.S. PATENT DOCUMENTS

| 5,424,303 | * | 6/1995 | Phan et al. ............................. 514/89 |
| 6,060,464 | | 5/2000 | Nguyen et al. ........................ 546/22 |

FOREIGN PATENT DOCUMENTS

| 0 559 079 A1 | 2/1993 | (EP) . |
| 0 703 239 A1 | 9/1995 | (EP) . |
| WO 97/02037 | 1/1997 | (WO) . |
| WO 98/28311 | 7/1998 | (WO) . |

* cited by examiner

*Primary Examiner*—Alan L. Rotman
(74) *Attorney, Agent, or Firm*—Wayne J. Dustman; William T. King; Charles M. Kinzig

(57) ABSTRACT

Aminophosphonates alpha substituted by phenol groups, of formula (I) have lipoprotein(a) lowering activity.

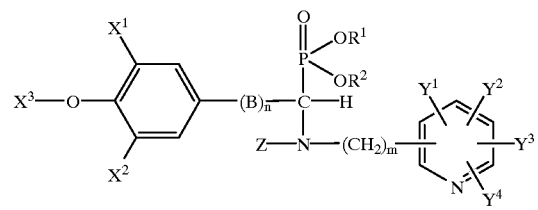

(I)

19 Claims, No Drawings

PHARMACEUTICAL AMINOPHOSPHONIC ACID DERIVATIVES

The present invention relates to novel aminophosphonate derivatives, processes for their preparations, pharmaceutical compositions containing them and their use in therapy, in particular for lowering lipoprotein(a) in plama and in tissues.

Lipoprotein(a) [Lp(a)] is a LDL-like lipoprotein where its major lipoprotein, apoB-100 is covalently linked to an unusual glycoprotein, apoprotein(a). Due to its structural similarity to plasminogen, apo(a) interferes with the normal physiological thrombosis-hemostasis process. The structural feature of Lp(a), where the LDL lipoprotein is linked to apo(a), is thought to be responsible for its atherogenic and thrombolytic activities.

Elevated levels of Lp(a) have been associated with the development of atherosclerosis, coronary heart disease, myocardial infarction, cerebral infarction, restenosis following balloon angioplasty and stroke. A recent epidemiologic study has provided the clinical proof of a positive correlation between plasma Lp(a) concentrations and the incidence of heart disease (see for instance: "Elevated Plasma Lipoprotein(a) and Coronary Heart Disease in Men Aged 55 Years and Younger"; A. G. Bostom, L. A. Cupples, J. L. Jenner, J. M. Ordovas, L. J. Seman, P. W. F. Wilson, E. J. Schaefer and W. P. Castelli; Journal of American Medical Association 1996, 276, p. 544–548.

Patients that have Lp(a) levels in excess of 20–30 mg/dl run a significantly increased risk of heart attacks and stroke. An effective therapy for lowering Lp(a) does not exist at present as potent hypocholesterolemic agents such as the HMGCoA reductase inhibitors do not affect Lp(a). Until recently, the only compound shown to lower Lp(a) was niacin. The high doses necessary for activity however entail unacceptable side-effects. There is therefore an unmet therapeutic need for agents that effectively reduce elevated levels of Lp(a).

International application WO97/02037 (Symphar SA; SmithKline Beecham plc, published Jan. 23, 1997), published after the priority date of the present application, describes a group of aminophosphonates alpha substituted by phenol groups of the formula (A):

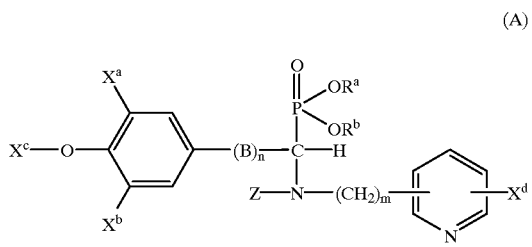

in which $X^a$ is H, $C_{(1-8)}$alkyl, hydroxy or $C_{(1-8)}$alkoxy; $X^b$ is $C_{(1-8)}$alkyl or $C_{(1-8)}$alkoxy; $X^c$ is H, $C_{(1-4)}$alkyl, or $X^3O$ and one of the two other substituents $X^a$ or $X^b$ may form an alkylidene dioxy ring having from 1 to 4 carbon atoms; $R^a$ and $R^b$ which may be identical or different, are H or $C_{(1-6)}$alkyl; B is $CH_2CH_2$, $CH=CH$, or $CH_2$; n is zero or 1; Z is H or a $C_{(1-8)}$alkyl group; m is 0 or an integer from 1 to 5; $X^d$ is H, or $C_{(1-8)}$alkyl, $C_{(1-8)}$alkoxy or halo; and the pyridyl ring is attached by the ring carbon α- or β- to the nitrogen (2- or 3-pyridyl). These have Lp(a) lowering activity. Compounds of formula (A) fall within scope of the generic disclosure of EP-A-0 559 079. This is directed towards aminophosponates alpha substituted by phenol groups which are said to be of use in decreasing plasma cholesterol and blood peroxides. Compounds of formula (A) are characterised by having either no substituents ($X^d$ is H) or a single substituent on the pyridyl ring. It has now been found that further substitution on the pyridyl ring provides compounds with an improved biological profile.

Accordingly, the present invention provides a compound of the formula (I):

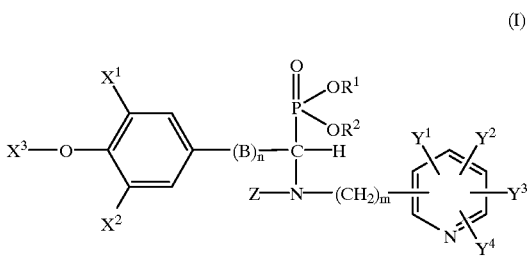

in which:

$X^1$ and $X^2$, which may be the same or different, are H, a straight or branched $C_{(1-8)}$alkyl or $C_{(1-8)}$alkoxy group, a hydroxy group or a nitro group;

$X^3$ is H, a $C_{(1-4)}$alkyl group, $X^3O$ and one of the two other substituents $X^1$ or $X^2$ may form a $C_{(1-4)}$alkylidene dioxy ring;

$R^1$ and $R^2$, which may be the same or different, are H, a straight or branched $C_{(1-6)}$alkyl group;

B is $CH_2$, $CH_2—CH_2$ or $CH=CH$;

n is zero or 1;

Z is H, or a straight or branched $C_{(1-8)}$alkyl group;

m is 0 or an integer from 1 to 5; and $Y^1$, $Y^2$, $Y^3$ and $Y^4$, which may be the same or different, are H, a straight or branched $C_{(1-8)}$alkyl or $C_{(1-8)}$alkoxy group, a cyano, trifluoromethyl, nitro, hydroxy, hydroxymethyl, $C_{(1-4)}$alkoxymethyl, amino, $C_{(1-4)}$alkylamino, $C_{(1-4)}$dialkylamino group, a halogen atom (F, Cl, Br, I), or any two adjacent $Y^1$, $Y^2$, $Y^3$ and $Y^4$ may form an optionally substituted $C_{(1-6)}$alkylidene or $C_{(1-4)}$alkylidenedioxy ring, with the proviso that at least two of the $Y^1$, $Y^2$, $Y^3$ and $Y^4$ groups are not H;

or a pharmaceutically acceptable salt thereof.

Preferably, $X^1$ is H, hydroxy, $C_{(1-4)}$alkyl or $C_{(1-4)}$alkoxy, preferably $C_{(1-3)}$alkyl or $C_{(1-3)}$alkoxy, more preferably hydrogen, hydroxy, methyl, methoxy or ethoxy.

Preferably, $X^2$ is $C_{(1-4)}$alkyl or $C_{(1-4)}$alkoxy, preferably $C_{(1-3)}$alkyl or $C_{(1-3)}$alkoxy, more preferably methyl, methoxy or ethoxy.

Preferably, $X^1$ and $X^2$ is each $C_{(1-4)}$alkyl, preferably $C_{(1-3)}$alkyl, or $C_{(1-4)}$alkoxy; or or one of $X^1$ and $X^2$ is $C_{(1-4)}$alkyl and the other is $C_{(1-4)}$alkoxy or $C_{(1-3)}$alkyl; or $X^1$ is hydroxy and $X^2$ is $C_{(1-4)}$alkyl or $C_{(1-4)}$alkoxy.

Preferred combinations of $X^1$ and $X^2$ include methoxy and methoxy, methoxy and methyl, ethoxy and methyl, methyl or t-butyl and methyl, ethoxy and ethoxy and ethoxy, hydroxy and methyl, and hydroxy and methoxy, respectively.

Preferably, $X^3$ is hydrogen or methyl.

A particularly preferred phenyl group is 4-hydroxy-3-methoxy-5-methylphenyl.

Preferably, $(B)_n$ is a direct bond.

Preferably, m is zero

Preferably, $R^1$ and $R^2$ is each a $C_{(1-3)}$alkyl group, more preferably, a $C_2$ or $C_3$ alkyl group, in particular $R^1$ and $R^2$ is ethyl or isopropyl.

Preferably, Z is hydrogen.

Representative values for $Y^1$ to $Y^4$ include alkyl, for instance methyl or t-butyl, methoxy, chloro, hydroxy, hydroxymethyl or two adjacent substituents form an optionally substituted alkylidene or alkyldenedioxy ring having 1 to 6 carbon atoms.

Preferably, $Y^1$ and $Y^2$ is each methyl, preferably as 2,6-substituents of the pyridyl ring, and $Y^3$ and $Y^4$ is each hydrogen,.

Preferably, the pyridyl ring is attached by the ring carbon β- to the nitrogen (3/5-pyridyl). A particularly preferred pyridyl ring is (2,6-dimethyl)pyrid-3-yl.

Pharmaceutically acceptable salts are well know in the art and include inorganic and organic salts, for instance salts with HCl, $H_2SO_4$, oxalic acid, maleic acid, sulfonic acid, etc.

Preferred compounds of formula (I) include:

Diisopropyl α-(4-hydroxy-3-methoxy-5-methylphenyl)-N-[3-(2,6-dimethylpyridyl)]-amino-methylphosphonate; and Diethyl α-(4-hydroxy-3-methoxy-5-methylphenyl)-N-[3-(2,6-dimethylpyridyl)]-amino-methylphosphonate;

and pharmaceutically acceptably salts;

in particular:

(+)-diisopropyl α-(4-hydroxy-3-methoxy-5-methylphenyl)-N-[3-(2,6-dimethylpyridyl)]-amino-methylphosphonate; and pharmaceutically acceptable salts thereof, in particular, the hydrochloride salt.

Compounds of formula (I) are found to be effective in decreasing Lp(a) production by primary cultures of Cynomolgus monkey hepatocytes. The Lp(a) of these primates is similar in immunologic properties to human Lp(a) and occurs in an almost identical frequency distribution of plasma concentrations (see "Plasma Lipoprotein(a) Concentration is Controlled by Apolipoprotein(a) Protein Size and the Abundance of Hepatic Apo(a) mRNA in a Cynomolgus Monkey Model", N. Azrolan et al, J. Biol. Chem., 266, 13866–13872, 1991). The compounds of formula (I) are thus potentially useful for decreasing Lp(a) in man and thereby providing a therapeutic benefit. Accordingly, in a further aspect, the present invention provides a compound of formula (I) or a pharmaceutically acceptable salt thereof for use in therapy, in particular as an Lp(a) lowering agent. Elevated plasma and tissue levels of lipoprotein(a) is associated with accelerated atherosclerosis, abnormal proliferation of smooth muscle cells and increased thrombogenesis and expressed in disease states such as, for instance: coronary heart disease, peripheral artery disease: intermittent claudication, thrombosis, restenosis after angioplasty, extracranial carotid atherosclerosis, stroke and atherosclerosis occuring after heart transplant. Compounds of formula (I) may also be useful in treating inflammatory diseases and excessive wound healing.

For such therapeutic use, the compounds of the present invention will generally be administered in a standard pharmaceutical composition. Accordingly, in a further aspect, the present invention provides for a pharmaceutical composition comprising a compound of formula (I) and a pharmaceutically acceptable excipient or carrier. Suitable excipients and carriers are well know in the art and will be selected with regard to the intended route of administration and standard pharmaceutical practice. For example, the compositions may be administered orally in the form of tablets containing such excipients as starch or lactose, or in capsule, ovules or lozenges either alone or in admixture with excipients, or in the form of elixirs or suspensions containing flavoring or coloring agents. They may be injected parentally, for example, intravenously, intramuscularly or subcutaneously. For parenteral administration, they are best used in the form of a sterile aqueous solution which may contain other substances, for example, enough salts or glucose to make the solution isotonic with blood. The choice of form for administration as well as effective dosages will vary depending, inter alia, on the condition being treated. The choice of mode of administration and dosage is within the skill of the art.

The compounds of formula (I) and their pharmaceutically acceptable salts which are active when given orally can be formulated as liquids, for example syrups, suspension or emulsions or as solids for example, tablets, capsules and lozenges. A liquid formulation will generally consist of a suspension or solution of the compound or pharmaceutically acceptable salt in suitable liquid carrier(s) for example, ethanol, glycerine, non-aqueous solvent, for example polyethylene glycol, oils, or water with a suspending agent preservative, flavoring or coloring agents. A composition in the form of a tablet can be prepared using any suitable pharmaceutical carrier(s) rountinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and the filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Typical parental compositions consists of a solution or suspension of the compound or pharmaceutically acceptable salt in a sterile aqueous carrier or parentally acceptable oil, for example polyethylene glycol, polyvinyl pyrrolidone, lecithin, arachis oil or sesame oil. Alternatively, the solution can be lyophilised and then reconstituted with a suitable solvent just prior to administration. A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit does form such as a tablet or capsule. Each dosage unit for oral administration contains preferably from 1 to 250 mg (and for parental administration contains preferably for 0.1 to 25 mg) of a compound of the structure (I) or a pharmaceutically acceptable salt thereof calculated as the free base.

The compounds of the invention will normally be administered to a subject in a daily dosage regimen. For an adult patient this may be, for example, an oral dose of between 1 mg and 500 mg, preferably between 1 and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day.

Compounds of formula (I) may be prepared by processes well know in the art, for instance those previously described in WO 97/02037.

Thus, for instance, compounds of formula (I) in which Z is hydrogen may be prepared by a process which comprises treating an imine of formula (II):

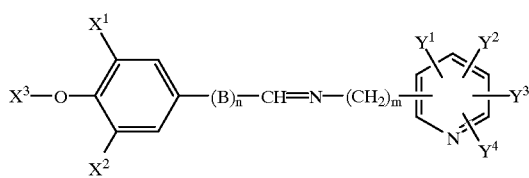

(II)

in which $X^1$, $X^2$, $X^3$, B, n, M, $Y^1$, $Y^2$, $Y^3$ and $Y^4$ are as previously defined; with a dialkyl phosphite of formula (III):

(III)

in which $R^1$ and $R^2$ are as previously defined; or a trialkyl silyl derivative thereof, preferably the trimethyl silyl phosphite, or a metal thereof, for instance the sodium salt, formed in situ by treatment of the compound of formula (III) with a suitable base, for instance sodium hydride, ethoxide or methoxide.

The reaction may be carried out in presence or absence of a catalyst. Suitable catalyst include an amine such as diethylamine or triethylamine. The reaction may be carried out in presence or in absence of a solvent. Suitable solvents include petroleum ether, benzene, toluene, diethyl ether, tetrahydrofuran, 1,2-dimethoxyethane. Suitable reaction temperatures are in the range of 30 to 140° C.

The imine compound of formula (II) may be obtained by condensing an aldehyde compound of formula (IV):

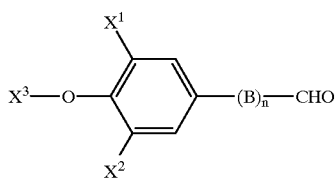

(IV)

in which $X^1$, $X^2$, $X^3$, B and n are as previously defined; with a primary amine of formula (V):

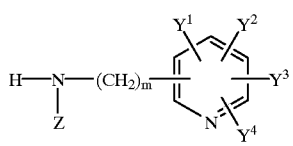

(V)

in which Z, m, $Y^1$, $Y^2$, $Y^3$ and $Y^4$ are as previously defined; under imine forming conditions.

Suitably, the condensation may be effected with or without a catalyst in a solvent such as ether, tetrahydrofuran, benzene, toluene or ethanol. Suitable catalyst include molecular sieve, an acid such as glacial acetic acid, p-toluenesulfonic acid, thionyl chloride, titanium tetrachloride, boron trifluoride etherate, or a base such as potassium carbonate. The reaction is suitably carried out in the range of 0° C. to the boiling point of the solvent being used. For less reactive amines or aldehydes, the reaction may be usefully carried out in a Dean-Stark apparatus.

Compounds of formula (I) may also be prepared by a process which comprises treating equimolar amounts of an aldehyde of formula (IV), and amine of formula (V) in which Z, m, $Y^1$, $Y^2$, $Y^3$ and $Y^4$ are as previously described; and a dialkyl phosphite of formula (III), suitably in the presence of p-toluenesulfonic acid as a catalyst, in a hydrocarbon solvent such as petroleum ether, benzene, toluene or xylene, at a temperature between ambient room temperature and the boiling point of the solvent being used, and with concomitant elimination of water, for instance, by using a Dean-Stark apparatus.

Compounds of formula (I) in which m is not zero may also be prepared by a process which comprises treating a compound in formula (VI)

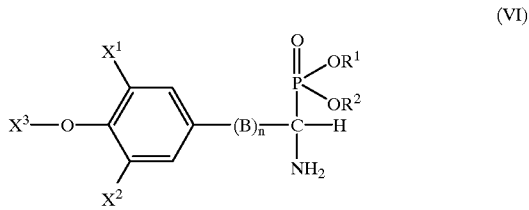

(VI)

in which $X^1$, $X^2$, $X^3$, B and n are previously defined; with an aldehyde of formula (VII):

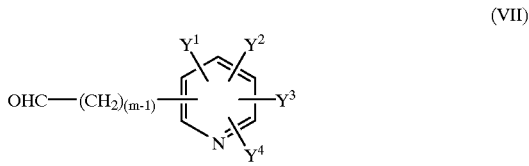

(VII)

in which m is an integer from 1 to 5 and $Y^1$, $Y^2$, $Y^3$ and $Y^4$ are as previously defined; under reductive amination conditions.

Suitable such conditions include carrying out the reaction in the presence of sodium cycanoborohydride in an alcoholic solvent, preferably methanol, at a pH between 3 to 6 and at a temperature between 0° C. and 25° C.

A compound of formula (VI) may be obtained according to the process previously described for a compound of formula (I) from an aldehyde of formula (IV), an amine of formula (VIII)

(VIII)

in which A is a protecting group which can be removed by a hydrogenolysis, for instance an α substituted benzyl or benzyloxycarbonyl and a phosphite of structure (III). This forms an intermediate which is then subjected to hydrogenolysis according to standard conditions, to give a compound of formula (VI).

It will be appreciated that the aminophosphonate ester of formula (I) have a basic centre and can form salts, for instance with inorganic acids such as HCl, $H_2SO_4$ and with organic acids such as oxalic acid, maleic acid, sulfonic acids, etc . . . All these salts are integral part of this invention.

Compounds of structure (I) are racemates as they have at least one chiral center which is carbon atom in position alpha to the phosphonate group. The compounds of formula (I) therefore exist in the two enantiomeric forms. The racemic mixtures (50% of each enantiomer), the pure enantiomers and other mixtures thereof all form part of the present invention. Mixtures of enantiomers, including racemates, may be resolved into its constituent enantiomer according to procedures well know in the art, including for instance, chiral chromatography. Unless otherwise indicated, the physical constants and biological data given for compounds of structure (I) refer to racemates.

The structure of compounds of formula (I) describe in the following Examples was established by their infrared (IR), mass (MS) and nuclear magnetic resonance (NMR) spectra. The purity of the compounds was checked by thin layer, gas liquid or high performance liquid chromatography.

The invention is further described in the following examples which are intended to illustrate the invention without limiting its scope.

The abbreviations used in this application are the following:

In the tables, n is normal, i is iso, s is secondary and t is tertiary. In the description of the NMR spectra, respectively 's' is singlet, 'd' is doublet, 'dd' is double doublet, 't' is triplet and 'm' is multiplet. TsOH is p-toluenesulfonic acid monohydrate. The temperatures were recorded in degrees Celsius and the melting points are not corrected.

EXAMPLES

Example 1

Diethyl α-(4-hydroxy-3,5-dimethylphenyl)-N-[3-(2,6-dimethylpyridyl)]-amino-methylphosphonate

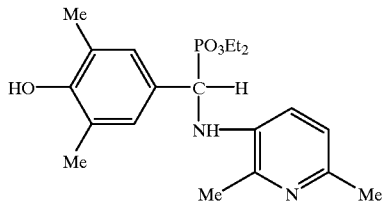

A mixture of 1.11 g (7.4 mmol) of 4-hydroxy-3,5-dimethylbenzaldehyde, 0.9 g (7.4 mmol) of 3-amino-2,6-dimethylpyridine, 3.05 g (22 mmol) diethylphosphite and ca 5 mg TsOH dissolved in 20 ml toluene contained in a flask connected to a Dean Stark apparatus was refluxed for 7 h. The solvent and the excess of diethylphosphite were evaporated to give a yellow oil which was purified by column chromatography ($SiO_2$, 95/5 $CHCl_3$/MeOH) to give 0.38 g (21%) of an oil which slowly solidified.

MS (m/e)=392: $M^+$, 255 (100%): $M^+$ —$PO_3Et_2$

NMR ($CDCl_3$):δ=7.0 (d, J=2 Hz, 2H): aromatic H, substituted phenyl; 6.73 and 6.61 (2m, 1H each): aromatic H, 3-pyridyl; 5.3 (1H): O$\underline{H}$; 4.55 (dd, J=7 and 22 Hz, 1H): C$\underline{H}$—$PO_3Et_2$; 4.49 (m, 1H): N—$\underline{H}$; 4.18 to 3.65 (m, 4H): P—O—C$\underline{H}_2$—$CH_3$; 2.49 and 2.36 (2s, 6H total): Py—C$\underline{H}_3$; 2.2 (1s, 6H): Ph—C$\underline{H}_3$; 1.29 and 1.15: (2t, J=7Hz, 6H total): P—O—$CH_2$—C$\underline{H}_3$

Example 2

Diethyl α-(3-tert-butyl-4-hydroxy-5-methylphenyl)-N-[3-(2,6-dimethylpyridyl)]-amino-methylphosphonate

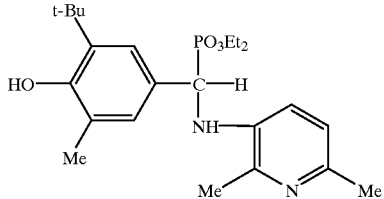

A mixture of 1.42 g (7.4 mmol) of 3-tert-butyl-4-hydroxy-5-methyl-benzaldehyde, 0.9 g (7.4 mmol) of 3-amino-2,6-dimethylpyridine, 3.05 g (22 mmol) diethylphosphite and ca 5 mg TsOH dissolved in 20 ml toluene contained in a flask connected to a Dean Stark apparatus was refluxed for 7 h. The solvent and the excess of diethylphosphite were evaporated and the residue was purified by column chromatography ($SiO_2$, 95/5 $CHCl_3$/MeOH) and recrystallization to give 0.89 g (21%) of a solid, mp=139–141° C.

MS (m/e)=434: $M^+$, 297 (100%): $M^+$ —$PO_3Et_2$

NMR ($CDCl_3$):δ=7.15 and 7.02 (2 m, 2H): aromatic H, substituted phenyl; 6.74 and 6.62 (2m, 1H each): aromatic H, 3-pyridyl; 5.15 (1H): O$\underline{H}$; 4.59 (dd, J=7 and 23 Hz, 1H): C$\underline{H}$—$PO_3Et_2$; 4.47 (m, 1H): N—$\underline{H}$; 4.18 to 3.65 (m, 4H): P—O—C$\underline{H}_2$—$CH_3$; 2.49 and 2.36 (2s, 6H total): Py—C$\underline{H}_3$; 2.18 (1s, 3H): Ph—C$\underline{H}_3$; 1.39 (s, 9H): t-Bu; 129 and 1.13: (2t, J=7Hz, 6H total): P—O—$CH_2$—C$\underline{H}_3$

Example 3

Diisopropyl α-(4-hydroxy-3-methoxy-5-methylphenyl)-N-[3-(2,6-dimethylpyridyl)]-amino-methylphosphonate

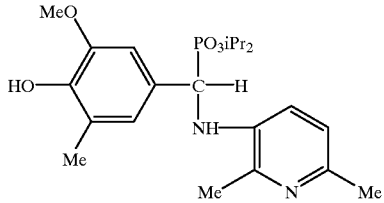

A mixture of 4.0 g (24 mmol) of 4-hydroxy-3-methoxy-5-methylbenzaldehyde, and 2.94 g (24 mmol) of 3-amino-2,6-dimethylpyridine dissolved in 40 ml toluene and a catalytic amount of p-toluenesulfonic acid (ca. 5 mg) contained in a flask connected to a Dean Stark apparatus was refluxed for 7 h. The solution was evaporated by dryness to give 6.5 g (100%) of an orange oil which was used for the next step. Diisopropyl phosphite (5.84 g, 35 mmol) was added to 3.8 g (14 mmol) of the crude imine dissolved in 40 ml toluene and a mixture was refluxed for 7 h. A further amount of diisopropyl phosphite (2.34 g, 14 mmol) was added and the mixture was refluxed for 2 more hours (total reaction time: 9 h). The solvent and the excess of diisopropyl phosphite were evaporated and the residue was purified by column chromatography ($SiO_2$, 95/5 $CHCl_3$/MeOH) and recrystallization (petroleum ether/$CH_2Cl_2$) to give 1.48 g (24%) of a tan solid, mp=138–139° C. A further recrystal lisation from a t-butyl methyl ether/CH$_2$Cl$_2$ mixture yielded a light yellow solid of analytical purity, mp=159–160° C.
Elemental analysis: C$_{22}$H$_{33}$N$_2$O$_5$P

| % Calc.  | C 60.54 | H 7.62 | N 6.47 | P 7.27 |
|----------|---------|--------|--------|--------|
| % Found  | C 60.45 | H 7.76 | N 6.35 | P 7.09 |

MS (m/e)=436: M$^+$, 271 (100%): M$^+$ —PO$_3$iPr$_2$
NMR (CDCl$_3$):δ=6.80 and 6.73 (2 m, 1H each): aromatic H, 3-pyridyl; 6,6 (m, 2H): aromatic H, substituted phenyl; 5.7 (1H): O$\underline{H}$; 4.65 and 4.47 (m, 2H): P—O—C$\underline{H}$—Me$_2$; 4.5 (2 overlapped m, 2H): C$\underline{H}$—PO$_3$iPr$_2$and N—$\underline{H}$; 3.85 (s, 3H): OC$\underline{H}_3$; 2.50 and 2.37 (2s, 6H total): Py—C$\underline{H}_3$; 2.22 (1s, 3H): Ph—C$\underline{H}_3$; 1.32, 1.29, 1.23 and 1.01: (4d, J=7Hz, 12H total): P—O—CH—(C$\underline{H}_3$)$_2$ This compound may also be prepared in 1,2-dimethoxyethane (DME). This imine (8.1 g, 0.03 mol) was dissolved in 10 ml DME and diisopropyl phosphite (7.5 g, 0.045 mol) was added and the resulting mixture was refluxed overnight. DME was evaporated under vacuum to give a material which was purified by column chromatography (95/5 CHCl$_3$/MeOH); the collected fractions gave after trituration in petroleum ether and two recrystallisations in CH$_2$Cl$_2$/MTBE 6.9 g (52%) of pure title compound, mp=159–160° C.

Alternately the reaction may be carried out neat (without solvent) in the phosphite reagent. To the crude imine (8.1 g, 0.03 mol) was added diisopropyl phosphite (7.5 g, 0.045 mol) and the homogenous brown mixture was heated at 120° C. for 2 hours. The oily reaction mixture was diluted in chloroform and extracted with a saturated bicarbonate solution. The dried organic phase was concentrated and triturated in petroleum ether to remove the excess of HPO$_3$iPr$_2$: a pasty solid was obtained. Column chromatography (95/5 CHCl$_3$/MeOH) and recrystallisation gave 6.5 g (50%) of the title compound, mp=159–160° C.

Example 4

Diethyl α-(4-hydroxy-3-methoxy-5-methylphenyl)-N-[3-(2,6-dimethylpyridyl)]-amino-methylphosphonate

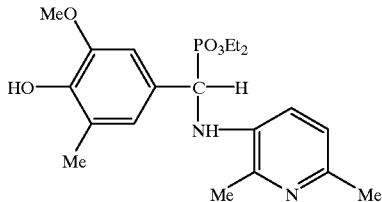

As described in Example 3, the imine (3.8 g, 14 mmol) obtained by condensing 4-hydroxy-3-methoxy-5-methylbenzaldehyde with 3-amino-2,6-dimethylpyridine was reacted with diethyl phosphite (5.82 g, 42 mmol) in 40 ml toluene at reflux temperature for 9 h to give 1.38 g (24%) of the title compound as a white solid, mp=145–147° C.
MS (m/e)=408: M$^+$, 271 (100%): M$^+$ —PO$_3$Et$_2$
NMR (CDCl$_3$):δ=6.82 and 6.76 (2 m, 2H each): aromatic H, 3-pyridyl; 6.6 (m, 2H): aromatic H, substituted phenyl; 5.7 (1H): O$\underline{H}$; 4.62–4.47 (2 overlapped m, 2H):C$\underline{H}$—PO$_3$Et$_2$and N—$\underline{H}$; 4.18 to 3.7 (m, 4H): P—O—C$\underline{H}_2$—C$\underline{H}_3$; 3.86 (s, 3H): OC$\underline{H}_3$; 2.52 and 2.39 (2s, 6H total): Py—C$\underline{H}_3$; 2.24 (1s, 3H): Ph—C$\underline{H}_3$; 1.31 and 1.19 (2t, J=7Hz, 6H total): P—O—CH$_2$—C$\underline{H}_3$ Example 5

Enantiomers of diisopropyl α-(4-hydroxy-3-methoxy-5-methylphenyl)-N-[3-(2,6-dimethylpyridyl)]-amino-methylphosphonate

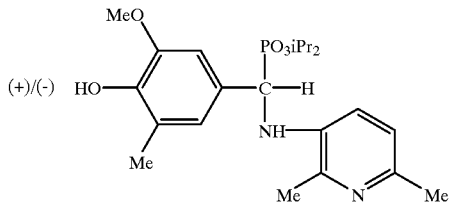

The enantiomers of a racemic mixture were separated by simulated moving bed chromatography using eight columns packed with 30 g of Chiralpak AD and hexane/ethanol (9/1) as the eluent. 42 g of the racemic mixture was processed to give after trituration with diethyl ether 16.1 g of the faster eluting enantiomer ([α]D25 +14.0° (c=1.0 EtOH), mp=123–124° C., optical purity=98.5%) and 15.2 g of the slower eluting enantiomer ([α]D25 −13.1° (c=1.0 EtOH), mp=120–122° C., optical purity=97.5%)

The structures of both enantiomers were confirmed by NMR, IR and MS spectroscopies and elemental analyses.

Elemental Analysis: C$_{22}$H$_{33}$N$_2$O$_5$P

| % Calc.         | C 60.54 | H 7.62 | N 6.47 |
|-----------------|---------|--------|--------|
| (+) Enantiomer  | C 60.57 | H 7.98 | N 6.40 |
| (−) Enantiomer  | C 60.45 | H 7.94 | N 6.32 |

Example 6

Hydrochloride salt of (+)diisopropyl α-(4-hydroxy-3-methoxy-5-methylphenyl)-N-[3-(2,6-dimethylpyridyl)]-amino-methylphosphonate

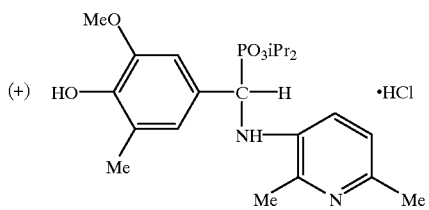

(+)Diisopropyl α-(4-hydroxy-3-methoxy-5-methylphenyl)-N-[3-(2,6-dimethylpyridyl)]-amino-methylphosphonate (1.5 g) was dissolved in 30 ml EtOH and cooled in an ice bath. A solution of HCl in Et$_2$O (1M, 3.45 ml) was added, after stirring for 10 min the mixture was concentrated under reduced pressure. The residue was crystallized from ethyl acetate to give 1.25 g of a white solid, [α]D25 +45.6° (c=0.535 EtOH), optical purity 99.9%.

Example 7

Hydrochloride salt of (-)diisopropyl α-(4-hydroxy-3-methoxy-5-methylphenyl)-N-[3-(2,6-dimethylpyridyl)]-amino-methylphosphonate

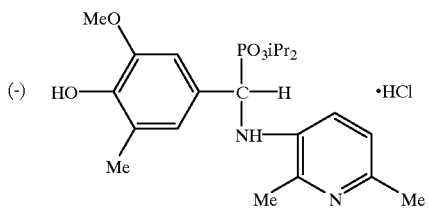

(-)Diisopropyl α-(4-hydroxy-3-methoxy-5-methylphenyl)-N-[3-(2,6-dimethylpyridyl)]-amino-methylphosphonate (1.11 g) was dissolved in 25 ml EtOH and cooled in an ice bath. A solution of HCl in Et$_2$O (1M, 2.54 ml) was added, after stirring for 10 min the mixture was concentrated under reduced pressure. The residue was crystallized from ethyl acetate to give 0.98 g of a white solid, [α]D25 −39.3° (c=0.595 EtOH), optical purity 94.0%.

Example 8

Diethyl α-(3,4-dimethoxy-5-methylphenyl)-N-[3-(2,6-dimethylpyridyl)]-amino-methylphosphonate

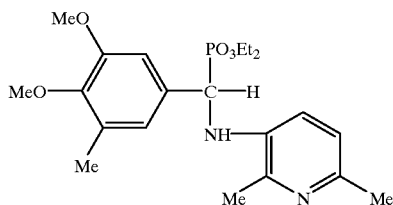

Methyl iodide (50 ml, 113.8 g, 0.8 mol) was added to mixture containing 16.6 g (0.1 mol) 4-hydroxy-3-methoxy-5-methyl-benzaldehyde, 55.2 g (0.4 mol) potassium carbonate in 90 ml methyl ethyl ketone and the resulting mixture was refluxed for 5 h. The solvent was evaporated on a rotary evaporator and the residue was partitioned between 100 ml H$_2$O and 100 ml CH$_2$Cl$_2$. The aqueous phase was further extracted by three 100 ml portions of CH$_2$Cl$_2$, the combined organic phases were dried over MgSO$_4$ and evaporated to give an orange oil weighing 18 g (100%). NMR (CDCl$_3$): α=9.83 (1H, CHO), 7.3 (2H, aromatic H), 3.92 and 3.90 (6H, OMe) and 2.33 (3H, Me).

A mixture of 1.62 g (9 mmol) of 3,4-dimethoxy-5-methylbenzaldehyde obtained as described above and 1.1 g (9 mmol) of 3-amino-2,6-dimethylpyridine dissolved in 25 ml toluene and a catalytic amount of p-toluenesulfonic acid (ca. 1 mg) contained in a flask connected to a Dean Stark apparatus was refluxed for 8 h. The solution was evaporated to dryness to give 2.56 g (100%) of an orange oil which was used directly for the next step.

Diethyl phosphite (3.73 g, 27 mmol) was added to 2.56 g (9 mmol) of the crude imine dissolved in 25 ml toluene and the mixture was refluxed for 8 h. The solvent and the excess of diethyl phosphite were evaporated and the residue was purified by column chromatography (SiO$_2$, 95/5 CHCl$_3$/MeOH) to give 2.7 g (71%) of a yellow oil.
MS (m/e)=423: M$^+$+1, 286 (100%): M$^+$+1 —PO$_3$Et$_2$
NMR (CDCl$_3$): δ=6.83 (m, 2H): aromatic H, substituted phenyl; 6.75 and 6.60 (2d, 1H each): aromatic H, 3-pyridyl; 4.62-4.47 (2 overlapped m, 2H): C$\underline{H}$—PO$_3$Et$_2$ and N—$\underline{H}$; 4.18 to 3.7 (m, 4H): P—O—C$\underline{H}_2$—CH$_3$; 3.83 and 3.78 (2s, 6H): OCH$_3$; 2.51 and 2.39 (2s, 6H total): Py—CH$_3$; 2.24 (1s, 3H): Ph—CH$_3$; 1.30 and 1.16: (2t, J=7Hz, 6H total): P—O—CH$_2$—C$\underline{H}_3$

Example 9

Diisopropyl α-(3,4-dimethoxy-5-methylphenyl)-N-[3-(2,6-dimethylpyridyl)]-amino-methylphosphonate

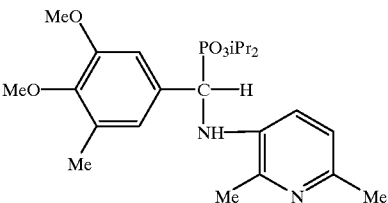

As described in Example 8, the imine (2.56 g, 9 mmol) obtained by condensing 3,4-dimethoxy-5-methylbenzaldehyde with 3-amino-2,6-dimethylpyridine was reacted with diisopropyl phosphite (4.49 g, 27 mmol) in 25 ml toluene at reflux temperature for 9 h to give 2.4 g (59%) of the title compound as a yellow oil, after purification by column chromatography (95/5 CH$_2$/MeOH).
MS (m/e)=451: M$^+$+1, 286 (100%): M$^+$+1 —PO$_3$iPr$_2$
NMR (CDCl$_3$): δ=6.81 (m, 2H): aromatic H, substituted phenyl; 6.75 and 6.65 (2m, 1H each): aromatic H, 3-pyridyl; 4.65-4.50 (m, 2H): P—O—C$\underline{H}$—Me$_2$; 4.5 (2 overlapped m, 2H): C$\underline{H}$—PO$_3$iPr$_2$ and N—$\underline{H}$; 3.82 and 3.76 (2s, 6H): OC$\underline{H}_3$; 2.50 and 2.38 (2s, 6H total): Py—C$\underline{H}_3$; 2.23 (1s, 3H): Ph—C$\underline{H}_3$; 1.32, 1.29, 1.23 and 1.01: (4d, J=7Hz, 12H total): P—O—CH$_2$—C$\underline{H}_3$)$_2$

Example 10

Diethyl α-(3-hydroxy-4-methoxy-5-methylphenyl)-N-[3-(2,6-dimethylpyridyl)]-amino-methylphosphonate

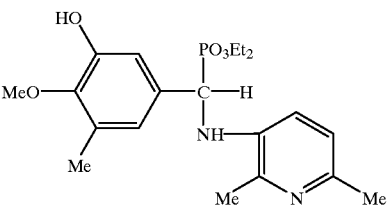

Anhydrous aluminum chlorides (5.3 g, 40 mmol) was suspended under nitrogen in a solution of 4-hydroxy-3-methoxy-5-methylbenzaldehyde (6 g, 36 mmol) in 40 ml dichloromethane. Pyridine (12.8 ml, 160 mmol) was added dropwise while stirring and cooling to maintain the temperature between 30 and 35° C. and the resulting orange solution was heated to reflux for 24 h. After cooling the reaction mixture was hydrolyzed with a 10% HCl solution until pH 1–2. The resulting two phases were separated, the dichloromethane phase was discarded and the aqueous phase was extracted with three 40 ml portions of diethyl ether. Evaporation of the dried ether phase gave 5.5 g (100%) of a beige solid which was identified as 3,4-dihydroxy-5-methylbenzaldehyde.

Methyl iodide (5.6 ml, 12.83 g, 90 mol) was added to mixture of 3,4-dihydroxy-5-methylbenzaldehyde, (55.5 g, 36 mol) and lithium carbonate (6.68 g, 90 mmol) in N,N-dimethylformamide (90 ml) and the resulting mixture was heated to 55° C. for 15 h. Another portion of methyl iodide (2 ml) was added and the mixture was kept at 55° C. for a further 4 h. The reaction mixture was poured into a mixture of 450 ml water and 10 ml 37% HCl, the aqueous phase was extracted with three portions of 150 ml diethyl ether. The solvent was evaporated and the residue was purified by column chromatography to give 2.8 g (47%) of an oil identified as 3-hydroxy-4-methoxy-5-methylbenzaldehyde. MS (m/e)=166 (100%): M$^+$, 151: M$^+$–Me; NMR (CDCl$_3$): δ=9.85 (1H, CHO), 7.32-7.82 (2H, aromatic H), 5.95 (1H, OH), 3.88 (3H, OMe) and 2.38 (3H, Me).

A mixture of 2.0 g (12 mmol) of 3-hydroxy-4-methoxy-5-methylbenzaldehyde obtained as described above and 1.47 g (12 mmol) of 3-amino-2,6-dimethylpyridine dissolved in 25 ml toluene and a catalytic amount of p-toluenesulfonic acid (ca. 1 mg) contained in a flask connected to a Dean Stark apparatus was refluxed for 4 h. The solution was evaporated to dryness to give 3.25 g (100%) of an brown solid which was used directly for the next step.

Diethyl phosphite (2.48 g, 18 mmol) was added to 1.63 g (6 mmol) of the crude imine dissolved in 25 ml toluene and the mixture was refluxed for 16 h. The solvent and the excess of diethyl phosphite were evaporated and the residue was purified by column chromatography (SiO$_2$, 95/5 CH$_2$Cl$_2$/MeOH) to give 0.9 g (37%) of a white solid, mp=141–142° C. after trituration in t-butyl methyl ether.
MS (m/e)=409: M$^+$+1, 272 (100%): M$^+$+1 —PO$_3$Et$_2$
NMR (CDCl$_3$): δ=8.0 (broad peak, 1H): OH; 6.82 and 6.74 (2m, 2H): aromatic H, substituted phenyl; 6.75 and 6.58 (2m, 1H each): aromatic H, 3-pyridyl; 4.56 (dd, J=7 and 24Hz, 1H): CH—PO$_3$Et$_2$; 4.43 (dd, J=7 and 10Hz, 1H): N—H; 4.16 to 3.71 (m, 4H): P—O—CH$_2$—CH$_3$; 3.80 (s, 3H): OCH$_3$; 2.39 (1s, 3H): Ph—CH$_3$; 2.28 (1s, 6H total): Py—CH$_3$; 1.29 and 1.16: (2t, J=7Hz, 6H total): P—O—CH$_2$—CH$_3$ Example 11

Diethyl α-(3-hydroxy-4-methoxy-5-methylphenyl)-N-[3-(2,6-dimethylpyridyl)]-amino-methylphosphonate

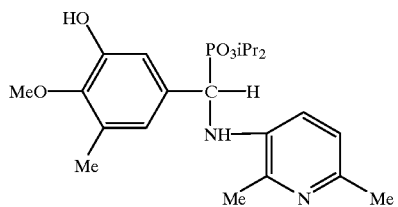

Diisopropyl phosphite (2.48 g, 18 mmol) was added to 1.63 g (6 mmol) of the crude imine dissolved in 25 ml toluene and the mixture was refluxed for 16 h. The solvent and the excess of diisopropyl phosphite were evaporated and the residue was purified by column chromatography (SiO$_2$, 95/5 CH$_2$Cl$_2$/MeOH) to give 1.1 g (42%) of a white solid, mp=168–169° C. after trituration in t-butyl methyl ether.
MS (m/e)=436: M$^+$271 (100%): M$^+$—PO$_3$iPr$_2$
NMR (CDCl$_3$): δ=7.9 (broad peak, 1H): OH; 6.83 and 6.74 (m, 2H): aromatic H, substituted phenyl; 6.74 and 6.58 (2d, 1H each): aromatic H, 3-pyridyl; 4.66 and 4.47 (2m, 2H): P—O—CH—Me$_2$; 4.54-4.45 (2 overlapped m, 2H): CH—PO$_3$iPr$_2$ and N—H; 3.79 (s, 3H): OCH$_3$; 2.38 (1s, 3H):Ph—CH$_3$; 2.29 and 2.27 (2s, 6H total): Py—CH$_3$; 1.31, 1.29, 1.22 and 1.01: (4d, J=7Hz, 12H total): P—O—CH$_3$—(CH$_3$)$_2$ Example 12

Diethyl α-(4,5-dimethoxy-3-hydroxyphenyl)-N-[3-(2,6-dimethylpyridyl)]-amino-methylphosphonate

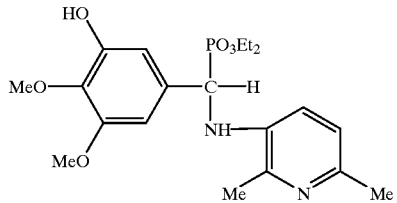

A mixture of 1.5 g (8 mmol) of 4,5-dimethoxy-3-hydroxybenzaldehyde and 0.98 g (8 mmol) of 3-amino-2,6-dimethylpyridine dissolved in 25 ml toluene and a catalytic amount of p-toluenesulfonic acid (ca. 1 mg) contained in a flask connected to a Dean Stark apparatus was refluxed for 16 h. The solution was evaporated to dryness to give 2.2 g (100%) of an oil which was used directly for the next step.

Diethyl phosphite (1.66 g, 12 mmol) was added to 1.15 g (4 mmol) of the crude imine dissolved in 25 ml toluene and the mixture was refluxed for 16 h. The solvent and the excess of diethyl phosphite were evaporated and the residue was purified by column chromatography (SiO$_2$, 95/5 CH$_2$Cl$_2$/MeOH) to give 0.52 g (30%) of a white solid, mp=134–136° C.
MS (m/e)=425: M$^+$+1, 288 (100%): M$^+$+1 —PO$_3$Et$_2$
NMR (CDCl$_3$): δ=7.2 (broad peak, 1H): OH; 6.76 and 6.60 (2d, 1H each): aromatic H, 3-pyridyl; 6.64 and 6.57 (m, 2H): aromatic H, substituted phenyl; 4.57 (dd, J=7 and 24Hz, 1H): CH—PO$_3$Et$_2$; 4.47 (dd, 1H): N—H; 4.18 to 3.76 (m, 4H): P—O—CH$_2$—CH$_3$; 3.87 and 3.84 (2s, 6H total): OCH$_3$; 2.39 and 2.38 (2s, 6H total): Py—CH$_3$; 1.30 and 1.19: (2t, J=7Hz, 6H total): P—O—CH$_2$—CH$_3$ Example 13

Diisopropyl α-(4,5-dimethoxy-3-hydroxyphenyl)-N-[3-(2,6-dimethylpyridyl)]-amino-methylphosphonate

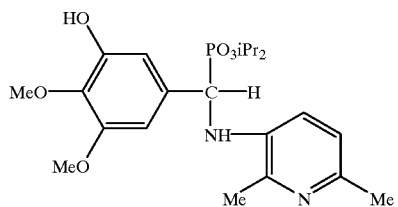

As described in Example 12, the imine (1.15 g, 4 mmol) obtained by condensing 4,5-dimethoxy-3-hydroxybenzaldehyde with 3-amino-2,6-dimethylpyridine was reacted with diisopropyl phosphite (2.0 g, 12 mmol) in 25 ml toluene at reflux temperature for 16 h to give 0.5 g (28%) of the title compound as a solid, mp=157–159° C. after purification by column chromatography (95/5 CH$_2$Cl$_2$/MeOH).
MS (m/e)=452: M$^+$, 287 (100%): M$^+$—PO$_3$iPr$_2$
NMR (CDCl$_3$): δ=6.9 (broad peak, 1H): OH; 6.76 and 6.59 (2d, 2H each): aromatic H, 3-pyridyl; 6.64 and 6.57 aromatic H, substituted phenyl; 4.69 and 4.51 (m, 2H): P—O—CH—Me$_2$; 4.5 (2 overlapped m, 2H): CH—PO$_3$iPr$_2$ and N—H; 3.86 and 3.85 (2s, 6H total): OCH$_3$; 2.41 and 2.38 (2s, 6H total): Py—CH$_3$; 1.33, 1.29, 1.23 and 1.04: (4d, J=7Hz, 12H total): P—O—CH—(CH$_3$)$_2$

Example 14

Diethyl α-(4-hydroxy-3-methoxy-5-methylphenyl)-N-[3-(2,6-dichloropyridyl)]-amino-methylphosphonate

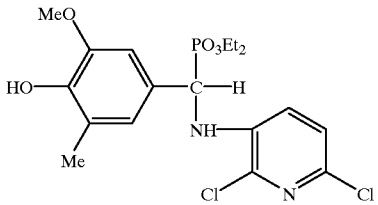

3-Amino-2,6-dichloropyridine (mp=118–120° C.) was obtained in quantitative yield by reacting 3-nitro-2,6-dichloropyridine with a mixture of reduced iron in aqueous acetic acid.

A mixture of 1.66 g (10 mmol) of 4-hydroxy-3-methoxy-5-methyl-benzaldehyde and 1.63 g (10 mmol) of 3-amino-2,6-dimethylpyridine dissolved in 40 ml toluene and a catalytic amount of p-toluenesulfonic acid (ca. 1 mg) contained in a flask connected to a Dean Stark apparatus was refluxed for 16 h.

Diethyl phosphite (3.45 g, 25 mmol) was added to toluene solution of the crude imine and the mixture was refluxed for 7 h. The solvent and the excess of diethyl phosphite were evaporated and the residue was purified by column chromatography ($SiO_2$, 95/5 $CH_2Cl_2$/MeOH) to give 0.52 g (30%) of a yellow solid.

MS (m/e)=448: $M^+(^{35}Cl)$, 311 (100%): $M^+(^{35}Cl)$ —$PO_3Et_2$
NMR ($CDCl_3$): δ=6.98 and 6.72 (2d, 1H each): aromatic H, 3-pyridyl; 6.77 (2m, 2H): aromatic H, substituted phenyl; 5.71 (1H): O$\underline{H}$; 5.36 (dd, J=7and 10Hz, 1H): N—$\underline{H}$; 4.53 (dd, J=7and 24Hz, 1H): C$\underline{H}$—$PO_3Et_2$; 4.18 to 3.73 (m, 4H): P—O—C$\underline{H}_2$—$CH_3$; 3.86 (s, 3H): OC$\underline{H}_3$; 2.23 (1s, 3H): Ph—C$\underline{H}_3$; 1.31 and 1.20: (2t, J=7Hz, 6H total): P—O—$CH_2$—C$\underline{H}_3$

Example 15

Diisopropyl α-(4-hydroxy-3-methoxy-5-methylphenyl)-N-[3-(2,6-dichloropyridyl)]-amino-methylphosphonate

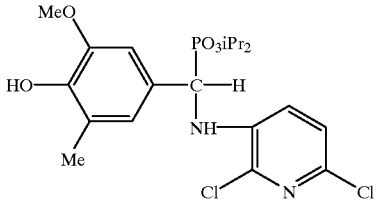

The process described in example 14 was followed using diisopropyl phosphite as reagent to give the title compound as a white solid, mp=124–125° C.
MS (m/e)=476: $M^+(^{35}Cl)$, 311 (100%): $M^+(^{35}Cl)$ —$PO_3iPr_2$
NMR ($CDCl_3$): δ=6.98 and 6.72 (2d, 1H): aromatic H, 3-pyridyl; 6.77 (m, 2H): aromatic H, substituted phenyl; 5.71 (1H): O$\underline{H}$; 5.36 (dd, J=7and 10Hz, 1H): N—$\underline{H}$; 4.67 to 4.50 (2m, 2H total): P—O—C$\underline{H}$—$Me_2$; 4.5 (overlapped m, 1H): C$\underline{H}$—$PO_3iPr_2$; 3.86 (s, 3H): OC$\underline{H}_3$; 2.23 (1s, 3H): Ph—C$\underline{H}_3$; 1.34, 1.31, 1.23 and 1.06: (4d, J=7Hz, 12H total) P—O—CH—$(CH_3)_2$

Example 16

Diethyl α-(3,5-dimethoxy-4-hydroxyphenyl)-N-[3-(2,6-dimethoxypyridyl)]-amino-methylphosphonate

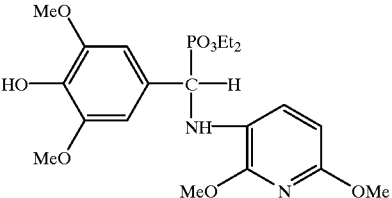

The imine (0.06 g, 2 mmol) obtained by condensing 3,5-dimethoxy-4-hydroxybenzaldehyde with 3-amino-2,6-dimethoxypyridine was reacted with diethyl phosphite (0.52 g, 4 mmol) in 25 ml toluene at reflux temperature for 5 h to give 0.34 g (40%) of the title compound as a brown oil, after purification by column chromatography (98/2 $CH_2Cl_3$/MeOH).

MS (m/e)=456: $M^+$, 319 : $M^+$—$PO_3Et_2$
NMR ($CDCl_3$): δ=6.68 (d, J=2Hz, 2H): aromatic H, substituted phenyl; 6.56 and 6.07 (d, J=8Hz, 2H): aromatic H, 3-pyridyl; 4.53 (d, J=23Hz, 1H): C$\underline{H}$—$PO_3Et_2$; ca 4.0 (overlapped m): N $\underline{H}$; 4.18 to 3.73 (m, 4H): P—O—C$\underline{H}_2$—$CH_3$; 3.98 and 3.81 (2s, 3H each): pyridyl—OC$\underline{H}_3$; 3.86 (1s, 6H): phenyl—OC$\underline{H}_3$; 1.29 and 1.19: (2t, J=7Hz, 6H total): P—O—$CH_2$—C$\underline{H}_3$

Example 17

Diethyl α-(3,5-di-tert-butyl-4-hydroxyphenyl-N-[4-(2,6-di-tert-butylpicolyl)]-amino-methylphosphonate

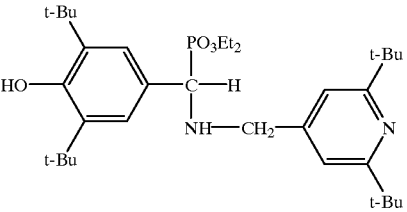

2,6-Di-tert-butylpyridine-4-carboxaldehyde was obtained by oxidation of 2,6-di-tert-butyl-4-methylpyridine with excess selenium dioxide in acetic acid at reflux temperature.

Diethyl α-(3,5-di-tert-butyl-4-hydroxyphenyl)-aminomethylphosphonate (1.67 g, 4.5 mmol) and 2,6-di-tert-butylpyridine-4-carboxaldehyde (1.8g, 8.2 mmol) in 25 ml of MeOH were reacted with $NaBH_3CN$ (0.85 g, 13 mmol) for 4 h. After neutralisation with diluted HCl the reacting mixture was extracted with $CH_2Cl_2$ and purified by column chromatography on silcagel ($CH_2Cl_2$/MeOH) to yield 1.1 g (43%) of the title compound; mp=132–137° C.;
MS (m/e)=573: $M^+$, 436 : $M^+$—$PO_3Et_2$
NMR ($CDCl_3$): δ=7.19 (d, J=2Hz, 2H): aromatic H, phenyl; 7.01 (s, 2H): aromatic H, 4-picolyl; 5.2 (s, 1H): OH; 4.15-3.77 (several m, 5 H): P—O—C$\underline{H}_2$—$CH_3$ and C$\underline{H}$—$PO_3Et_2$; 3.75 and 3.54 (2d, J=14 Hz): NH—C$\underline{H}_2$—Py 1.44 and 1.33 (2s, 9H each): phenyl-tert-butyl and pyridyl-tert-butyl; 1.29 and 1.10 (2t, J=7Hz, 6H): P—O—$CH_2$—C$\underline{H}_3$

Example 18

Hydrochloride salt of diisopropyl α-(4-hydroxy-3-methoxy-5-methylphenyl)-N-[3-(2,6-dimethylpyridyl)]-amino-methylphosphonate

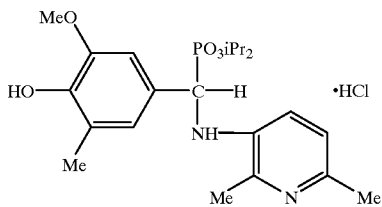

Diisopropyl α-(4-hydroxy-3-methoxy-5-methylphenyl)-N-[3-(2,6-dimethylpyridyl)]-amino-methylphosphonate (4.2 g, 9.6 mmol) was suspended in 20 ml diethylether and cooled in an ice bath. A solution of HCl in $Et_2O$ (1M, 17.5 ml) was added, after stirring for 45 min the mixture was evaporated under reduced pressure until constant weight. An amount of 4.1 g (90%) of a yellow solid was obtained. Elemental analysis: $C_{22}H_{34}ClN_2O_5P$

| % Calc. | C 55.87 | H 7.25 | Cl 7.50 | N 5.92 | P 6.55 |
|---|---|---|---|---|---|
| % Found | C 54.01 | H 7.42 | Cl 7.54 | N 5.73 | P 6.22 |

Example 19

Enantiomers of diethyl α-(4-hydroxy-3-methoxy-5-methylphenyl)-N-[3-(2,6-dimethylpyridyl)]-amino-methylphosphonate

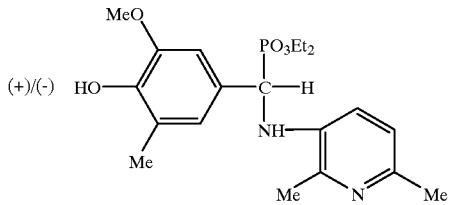

Racemic compound (Example 4) was resolved into its two enantiomers by chiral chromatography, using the following conditions:

Column: Chiralpak AD, 250 mm×20 mm i.d
Mobile Phase: 85/15 Hexane/Ethanol v/v
Flow Rate: 10 ml/min
Detection: UV at 215 nm
Sample Concentration: 50 mg dissolved in 10 ml of 50/50 Hexane/Ethanol v/v
Injection Volume: 500 μl Under these conditions, the first eluting enantiomer peak eluted at 14.7 minutes and the second eluting peak eluted at 18.6 minutes. The two peaks were just baseline resolved. The two peaks were collected as separate fractions over a number of injections. A small sample of each enantiomer fraction was removed for chiral analysis to determine the enantiomeric purity of each fraction. The HPLC conditions used for this chiral analysis were as follows:

Column: Chiralpak AD, 250 mm×4.6 mm i.d
Mobile Phase: 85/15 Hexane/Ethanol v/v
Flow Rate: 1 ml/min
Detection: UV at 215 nm
Injection Volume: 20 μl
Sample Concentration: Unknown—sample of undried peak fraction used.

Under these conditions the main peak of the first eluting enantiomer fraction eluted at 6.95 minutes. No peak due to the minor enantiomer was observed in this fraction. The main peak of the second eluting enantiomer fraction eluted at 6.85 minutes with a small peak due to the minor enantiomer also observed eluting at 7.1 minutes and representing 0.3% of the total enantiomer peak area.

The remainder of each enantiomer fraction was dried on a rotary evaporator. Each fraction has then been resuspended in a few mls ethanol and transferred to a small prewieghed vial. The samples were blown to dryness under nitrogen at present prior to measurement of their mass spec and optical rotation.

$M^{30}H$ for each enatiomer=409.1

First eluting enantiomer: $[\alpha]^D$ at 25° C.=+7.93°(c=1.19% EtOH)

Second eluting enantiomer: $[\alpha]^D$ at 2520 C.=−8.29°(c=1.09% EtOH)

Example 20

Dimethyl α(4-hydroxy-3-methoxy-5-methylphenyl)-N-[3-(2,6-dimethylpyridyl)]-amino-methylphosphonate Dimethyl phosphite (0.4 g, 3.7 mmol) was added to 0.5 g (1.85 mmol) of the crude imine (obtained as described in example 3) and the mixture was heated to 120° C. for 2h. The oily reaction mixture was diluted in chloroform and extracted with a saturated bicarbonate solution. The dried organic phase was concentrated and triturated in petroleum ether to remove the excess of dimethyl phosphite. Further purification by column chromatography ($SiO_2$, 95/5 $CHCl_3$/MeOH) and recrystallization (petroleum ether/$CH_2$ $Cl_2$) gave 0.25 g (34%) of a solid, mp=166–168° C.

IR (KBr)=3300 cm −1: NH, 1240: P=O, 1030: P—O—C

Further compounds of formula (I) were prepared by following procedures anologous to those described in the foregoing examples. The are included in the following Table 1, along with the preceding examples. The left hand column refers to a 'Compound' rather than the Example number, the same compound numbers being then used in the Biological Data section.

TABLE 1

Aminophosphonates of formula (I) (where n is 0 and $R^1$, $R^2$ are identical)

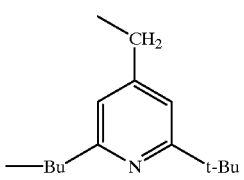

| Cpd No | Ex No | $X^1$ | $X^2$ | $X^3$ | Z | (CH₂)ₘ—[ring with Y¹,Y²,Y³,Y⁴,N] | $R^1$, $R^2$ | mp (° C.) |
|---|---|---|---|---|---|---|---|---|
| 1 |  | OMe | OMe | H | H | 3-(2,6-dimethyl)pyridyl | Et | 152–154 |
| 2 | 4 | OMe | Me | H | H | 3-(2,6-dimethyl)pyridyl | Et | 145–147 |
| 3 | 3 | OMe | Me | H | H | 3-(2,6-dimethyl)pyridyl | iPr | 159–160 |
| 4 | 1 | Me | Me | H | H | 3-(2,6-dimethyl)pyridyl | Et | solid |
| 5 | 2 | tBu | Me | H | H | 3-(2,6-dimethyl)pyridyl | Et | 139–141 |
| 6 |  | OEt | Me | H | H | 3-(2,6-dimethyl)pyridyl | Et | 125–127 |
| 7 |  | OEt | Me | H | H | 3-(2,6-dimethyl)pyridyl | iPr | 145–146 |
| 8 | 17 | tBu | tBu | H | H | 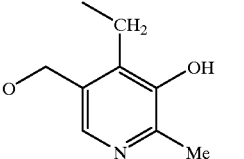 | Et | 132–137 |
| 9 |  | tBu | tBu | H | H | 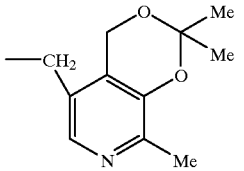 | Et | 139–145 |
| 10 |  | tBu | tBu | H | H | [dioxane-fused pyridine structure] | Et | 78–90 |
| 11 |  | tBu | tBu | H | H | 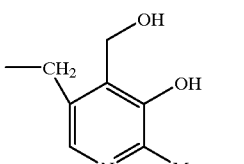 | Et | 172–176 |
| 12 | 8 | OMe | Me | Me | H | 3-(2,6-dimethyl)pyridyl | Et | oil |
| 13 | 9 | OMe | Me | Me | H | 3-(2,6-dimethyl)pyridyl | iPr | oil |
| 14 | 10 | OH | Me | Me | H | 3-(2,6-dimethyl)pyridyl | Et | 141–142 |
| 15 | 11 | OH | Me | Me | H | 3-(2,6-dimethyl)pyridyl | iPr | 168–169 |
| 16 | 12 | OH | OMe | Me | H | 3-(2,6-dimethyl)pyridyl | Et | 134–136 |
| 17 | 13 | OH | OMe | Me | H | 3-(2,6-dimethyl)pyridyl | iPr | 157–159 |
| 18 | 14 | OMe | Me | H | H | 3-(2,6-dichloro)pyridyl | Et | solid |
| 19 | 15 | OMe | Me | H | H | 3-(2,6-dichloro)pyridyl | iPr | 124–125 |
| 20 | 16 | OMe | OMe | H | H | 3-(2,6-dimethoxy)pyridyl | Et | oil |
| 21* | 5 | OMe | Me | H | H | 3-(2,6-dimethyl)pyridyl | iPr | 123–124 |
| 22* | 5 | OMe | Me | H | H | 3-(2,6-dimethyl)pyridyl | iPr | 120–122 |
| 23* | 19 | OMe | Me | H | H | 3-(2,6-dimethyl)pyridyl | Et | ? |
| 24* | 19 | OMe | Me | H | H | 3-(2,6-dimethyl)pyridyl | Et | ? |

*Cpd 21 - (+) Enantiomer of Cpd 3; Cpd 22 - (−) Enantiomer of Cpd 3; Cpd 23 - (+) Enantiomer of Cpd 2; Cpd 24 - (−) Enantiomer of Cpd 2

Biological Data

The compounds of formula (I) were assayed for lowering the production of Lp(a) in primary cultures of Cynomolgus hepatocytes.

Assay

Hepatocytes were isolated from livers of adult Cynomolgus monkeys by the two-step collagenase perfusion method according to C. Guguen-Guillouzo and A. Guillouzo "Methods for preparation of adult and fetal hepatocytes" p. 1–12 in "Isolated and Cultured Hepatocytes", les editions Inserm Paris and John Libbey Eurotext London (1986).

The viability of cells was determined by Trypan blue staining. The cells were then seeded at a density from 0.7. $10^5$ to $1.10^5$ viable cells per cm² in tissue culture plates in Williams E tissue culture medium containing 10% fetal calf serum. Cells were incubated for 4–6 hours at 37° C. in a $CO_2$ incubator (5% $CO_2$) in the presence of 20μM of the test compounds dissolved in ethanol. Four to six wells were used for each compound. Nicotinic acid and steroid hormones were used as references to validate the assay system since the are known to decrease Lp(a) in man. Control cells were incubated in the presence of ethanol only Results LP(a) Concentration The amount of Lp(a) secreted in culture medium was directly assayed by ELISA using a commercially available kit. Cells were washed and lysed as described by A. L. White et al, Journal of Lipid Research vol 34, p. 509–517, (1993) and the cellular content of Lp(a) was assayed as described above.

Changes in Lp(a) concentration in culture medium are given as the percentage of values measured for the control plates at 24 h.

All compound were tested at 20 μM. Compounds No. 1, 2, 3, 4, 5, 6, 7, 15, 16, 21 and 22 were found to decrease the Lp(a) secretion by 20% to 50%. Compounds 12, 13, 14, 17, 18, and 19 lowered the Lp(a) secretion by 13 to 20%.

(b) In vivo Results

Study Protocol

Male cynomolgus monkeys weighing between 3 and 7 kg were divided into groups of 3 to 4 animals each. Prior to treatment their plasma Lp(a) levels followed over a two-month period to ascertain a constant baseline value. The Lp(a) values measured at Day-7 and Day-1 were comparable and served as predose values. Test compounds were given orally in gelatin capsules by gavage at the dose of 25 mg/kg/day for 4 weeks and Lp(a) was measured at weekly intervals (Day 7, 4, 21 and 28). At the end of the dosing period, animals were maintained for a treatment free period of 4 weeks, whereupon their plasma Lp(a) levels returned to pretreatment levels. This control provided proof that the decrease in Lp(a) measured was caused by the pharmacological activity of the test compounds.

Results

At Days--7, -1,7, 14, 21 and 28, after an overnight fast blood samples were collected on EDTA and Lp(a) was measured by the highly sensitive and specific ELISA test. Results (mean of 3–4 values of each group were expressed as % of predose values. Selected compounds of formula (I) were tested under the experimental conditions to investigate their pharmacological activity in vivo.

Compounds No 2, 3 and 6 were tested to 25 mg/kg/day for 28 days and lowered plasma Lp(a) in the range of 15% to 27% (values measured at Day 28, % change from predose values). Compounds 21 and 22 were tested at 50 mg/kg/day for 10 days and decreased plasma Lp(a) in the range of 13 to 39% (values measured at Day 10, % change from predose values).

What is claimed is:
1. A compound structure (I):

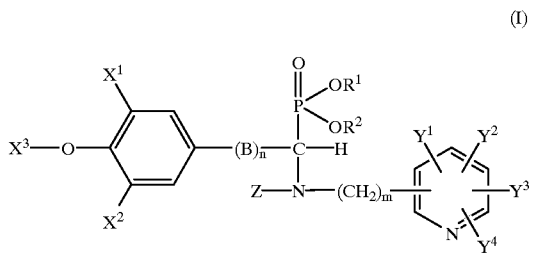

in which:
X¹ and X², which may be the same or different, are H, a straight or branched $C_{(1-8)}$alkyl or $C_{(1-8)}$alkoxy group, a hydroxy group or a nitro group;
X³ is H, a $C_{(1-4)}$alkyl group, X³O and one of the two other substituents X¹ and X² may form a $C_{(1-4)}$alkylidene dioxy ring;
R¹ and R², which may be the same or different, are H, a straight or branched $C_{(1-6)}$alkyl group;
B is $CH_2$, $CH_2-CH_2$ or $CH=CH$;
n is zero or 1;
Z is H, or a straight or branched $C_{(1-8)}$alkyl group;
m is 0 or an integer 1 to 5; and
Y¹, Y², Y³ and Y⁴, which may be the same or different, are H, a straight or branched $C_{(1-8)}$alkyl or $C_{(1-8)}$alkoxy group, a cyano, trifluoromethyl, nitro, hydroxy, hydroxymethyl, $C_{(1-4)}$ alkoxymethyl, amino $C_{(1-4)}$ alkylamino, $C_{(1-4)}$dialkylamino group, or any two adjacent Y¹, Y², Y³ and Y⁴ may form an optionally substituted $C_{(1-6)}$alkylidene or $C_{(1-4)}$alkylidenedioxy ring, with the proviso that at least two of the Y¹, Y², Y³ and Y⁴ groups are not H;
or a pharmaceutically acceptable salt thereof.
2. A compound as claimed in claim 1 in which X¹ is H, hydroxy, $C_{(1-4)}$alkyl or $C_{(1-4)}$alkoxy.
3. A compound as claimed in claim 1 in which X² is $C_{(1-4)}$alkyl or $C_{(1-4)}$alkoxy.
4. A compound as claimed in claim 1 in which X¹ and X² is each $C_{(1-4)}$alkyl or $C_{(1-4)}$alkoxy; or one of X¹ and X² is $C_{(1-4)}$alkyl and the other is $C_{(1-4)}$alkoxy or $C_{(1-3)}$alkyl; or X¹ is hydroxy and X² is $C_{(1-4)}$alkyl or $C_{(1-4)}$alkoxy.
5. A compound as claimed in claim 1 in which X¹ and X² are methoxy and methoxy, methoxy and methyl, ethoxy and methyl, methyl or t-butyl and methyl, ethoxy and ethoxy, hydroxy and methyl, and hydroxy and methoxy, respectively.
6. A compound as claimed in claim 1 in which X³ is hydrogen or methyl.
7. A compound as claimed in claim 1 in which $(B)_n$ is a direct bond.
8. A compound as claimed in claim 1 in which Z is hydrogen.
9. A compound as claimed in claim 1 in which Y¹ and Y² is each methyl and Y³ and Y⁴ is each hydrogen.
10. A compound as claimed in claim 1 in which the pyridyl ring is attached by the ring carbon β- to the nitrogen (3/5-pyridyl).
11. A compound as claimed in claim 1 in which m is zero.
12. A compound of formula (I) as defined in claim 1 selected from:
diethyl α-(4-hydroxy-3,5-dimethoxyphenyl)-N-[3-(2,6-dimethylpyridyl)]-aminomethylphosphonate;

diethyl α-(4-hydroxy-3,5-dimethylphenyl)-N-[3-(2,6-dimethylpyridyl)]-aminomethylphosphonate;

diethyl α-(3-tert-butyl-4-hydroxy-3-methylphenyl)-N-[3-(2,6-dimethylpyridyl)]-aminomethylphosphonate;

diethyl α-(3-ethoxy-4-hydroxy-5-methylphenyl)-N-[3-(2,6-dimethylpyridyl)]-aminomethylphosphonate;

diisopropyl α-(3-ethoxy-4-hydroxy-5-methylphenyl)-N-[3-(2,6-dimethylpyridyl)]-aminomethylphosphonate;

diethyl α-(3,5-di-tert-butyl-4-hydroxyphenyl)-N-[4-(2,6-di-tert-butylpicolyl)]-aminomethylphosphonate;

diethyl α-(3,5-di-tert-butyl-4-hydroxyphenyl)-N-[4-(3-hydroxy-5-hydroxymethyl-2-methylpicolyl)]-aminomethylphosphonate;

diethyl α-(3,5-di-tert-butyl-4-hydroxyphenyl)-N-[5-(3,4-O-isopropylidene-3-hydroxy-4-hydroxymethyl-2-methylpicolyl)]-aminomethylphosphonate;

diethyl α-(3,5-di-tert-butyl-4-hydroxyphenyl)-N-[5-(3-hydroxy-4-hydroxymethyl-2-methylpicolyl)]-aminomethylphosphonate;

diethyl α-(3,4-dimethoxy-5-methylphenyl)-N-[3-(2,6-dimethylpyridyl)]-aminomethylphosphonate;

diisopropyl α-(3,4-dimethoxy-5-methylphenyl)-N-[3-(2,6-dimethylpyridyl)]-aminomethylphosphonate;

diethyl α-(3-hydroxy-4-methoxy-5-methylphenyl)-N-[3-(2,6-dimethylpyridyl)]-aminomethylphosphonate;

diisopropyl α-(3-hydroxy-4-methoxy-5-methylphenyl)-N-[3-(2,6-dimethylpyridyl)]-aminomethylphosphonate;

diethyl α-(4,5-dimethoxy-3-hydroxyphenyl)-N-[3-(2,6-dimethylpyridyl)]-aminomethylphosphonate;

diisopropyl α-(4,5-dimethoxy-4-hydroxyphenyl)-N-[3-(2,6-dimethylpyridyl)]-aminomethylphosphonate; and diethyl α-(3,5-dimethoxy-4-hydroxyphenyl)-N-[3-(2,6-dimethylpyridyl)]-aminomethylphosphonate; or a pharmaceutically acceptable salt thereof.

13. A compound of formula (I) as defined in claim 1 selected from:

diisopropyl α-(4-hydroxy-3-methoxy-5-methylphenyl)-N-[3-(2,6-dimethylpyridyl)]-aminomethylphosphonate;

(+)diisopropyl α-(4-hydroxy-3-methoxy-5-methylphenyl)-N-[3-(2,6-dimethylpyridyl)]-aminomethylphosphonate;

(−)diisopropyl α-(4-hydroxy-3-methoxy-5-methylphenyl)-N-[3-(2,6-dimethylpyridyl)]-aminomethylphosphonate;

diethyl α-(4-hydroxy-3-methoxy-5-methylphenyl)-N-[3-(2,6-dimethylpyridyl)]-aminomethylphosphonate;

(+)diethyl α-(4-hydroxy-3-methoxy-5-methylphenyl)-N-[3-(2,6-dimethylpyridyl)]-aminomethylphosphonate; and (−)diethyl α-(4-hydroxy-3-methoxy-5-methylphenyl)-N-[3-(2,6-dimethylpyridyl)]-aminomethylphosphonate; or a pharmaceutically acceptable salt thereof, in particular the hydrochloride salt.

14. A pharmaceutical composition comprising a compound of formula (I) as defined in claim 1 and a pharmaceutically acceptable excipient thereof.

15. A method of treating a disease associated with elevated plasma and tissue lipoprotein(a) levels which method comprises administering to a patient in need thereof a therapeutically effective amount of a compound of formula (I) as defined in claim 1, or a pharmaceutically acceptable salt thereof.

16. A method of treating thrombosis by decreasing plasma lipoprotein(a) levels which method comprises administering to a patient in need thereof therapeutically effective amount of a compound of formula (I) as defined in claim 1, or a pharmaceutically acceptable salt thereof.

17. A method of treating restenosis following angioplasty by decreasing plasma lipoprotein(a) levels which method comprises administering to a patient in need thereof a therapeutically effective amount of a compound of formula (I) as defined in claim 1, or a pharmaceutically acceptable salt thereof.

18. A method of treating atheroslerosis by decreasing plasma lipoprotein(a) levels which method comprises administering to a patient in need thereof a therapeutically effective amount of a compound of formula (I) as defined in claim 1, or a pharmaceutically acceptable salt thereof.

19. A process for preparing a compound of formula (I) as defined in claim 1 which process comprises:

(a) for compounds of formula (I) in which Z is hydrogen, treating an imine of formula (II):

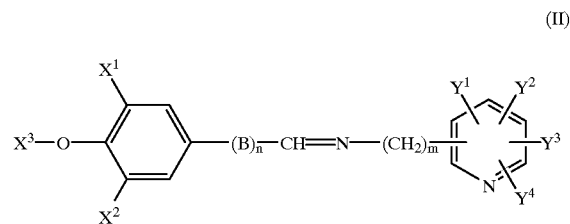

in which $X^1$, $X^2$, $X^3$, B, n, m, $Y^1$, $Y^2$, $Y^3$ and $Y^4$ are as define in claim 1; with a dialkyl phosphite of formula (III):

in which $R^1$ and $R^2$ are as defined in claim 1, or a trialkyl silyl or metal derivative thereof;

(b) reacting together equimolar amounts of an aldehyde of formula (IV):

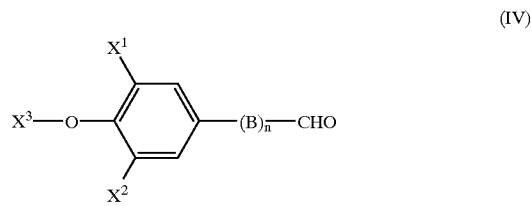

in which $X^1$, $X^2$, $X^3$, B and n are as defined in claim 1; an amine of formula (V):

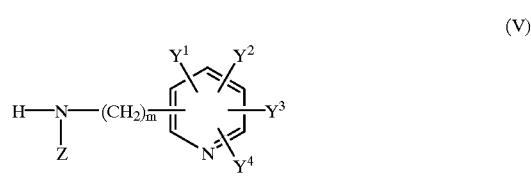

in which Z, m, $Y^1$, $Y^2$, $Y^3$ and $Y^4$ are as previously defined; and a dialkyl phosphite of formula (III; or (c) for compounds of formula (I) in which m is not zero, treating a compound of formula (VI)

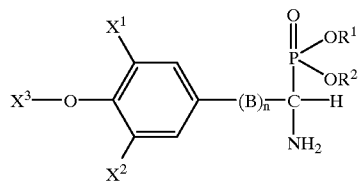
(VI)
in which $X^1$, $X^2$, $X^3$, B and n are as defined in claim 1, with an aldehyde of formula (VII):
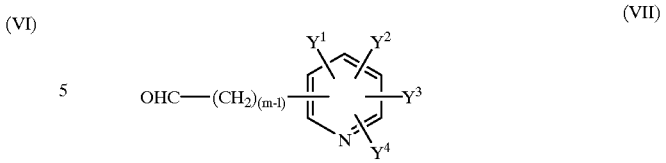
(VII)
in which m is an integer from 1 to 5 and $Y^1$, $Y^2$, $Y^3$ and $Y^4$ are as defined in claim 1, under reductive amination conditions.
* * * * *

UNITED STATES PATENT AND TRADEMARK OFFICE
CERTIFICATE OF CORRECTION

PATENT NO.   : 6,303,784 B1
DATED        : October 16, 2001
INVENTOR(S)  : Nguyen et al.

It is certified that error appears in the above-identified patent and that said Letters Patent is hereby corrected as shown below:

<u>Column 23,</u>
Line 32, please delete "α-(4,5-dimethoxy-4-hydroxyphenyl)-N-[3-" and insert -- α-(4,5-dimethoxy-3-hydroxyphenyl)-N-[3- -- therefor.

Signed and Sealed this

Twenty-first Day of October, 2003

JAMES E. ROGAN
*Director of the United States Patent and Trademark Office*